(12) United States Patent
Akhverdian et al.

(10) Patent No.: US 7,186,531 B2
(45) Date of Patent: Mar. 6, 2007

(54) **L-THREONINE PRODUCING BACTERIUM BELONGING TO THE GENUS *ESCHERICHIA* AND METHOD FOR PRODUCING L-THREONINE**

(75) Inventors: Valery Zavenovich Akhverdian, Moscow (RU); Ekaterina Alekseevna Savrasova, Moscow (RU); Alla Markovna Kaplan, Moscow (RU); Andrey Olegovich Lobanov, Moscow (RU); Yuri Ivanovich Kozlov, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/002,072

(22) Filed: Dec. 3, 2004

(65) Prior Publication Data
US 2005/0124048 A1 Jun. 9, 2005

Related U.S. Application Data

(60) Provisional application No. 60/586,222, filed on Jul. 9, 2004.

(30) Foreign Application Priority Data
Dec. 5, 2003 (RU) ............................ 2003135292

(51) Int. Cl.
*C12P 13/04* (2006.01)
*C12P 13/08* (2006.01)
*C12P 21/06* (2006.01)
*C12N 9/02* (2006.01)
*C12N 1/21* (2006.01)
*C12N 15/70* (2006.01)
*C07H 21/04* (2006.01)

(52) U.S. Cl. .................. 435/106; 435/115; 435/320.1; 435/189; 435/6; 435/252.33; 435/69.1; 536/23.2

(58) Field of Classification Search .............. 435/115, 435/252.33, 69.1, 320.1; 536/23.2
See application file for complete search history.

(56) References Cited

U.S. PATENT DOCUMENTS 5,175,107 A 12/1992 Debabov et al. ........ 435/252.33
6,040,160 A 3/2000 Kojima et al. .............. 435/115
6,297,031 B1 10/2001 Debabov et al. ............ 435/115
6,653,111 B2 11/2003 Debabov et al. ............ 435/115
2001/0049126 A1 12/2001 Livshits et al. ............. 435/106
2003/0148473 A1 8/2003 Livshits et al. ............. 435/108
2004/0038380 A1 2/2004 Debabov et al. ............ 435/115
2004/0132165 A1 7/2004 Akhverdian et al. ........ 435/252
2004/0229320 A1 11/2004 Stoynova et al. ........... 435/106
2004/0229321 A1 11/2004 Savrasova et al. .......... 435/106

FOREIGN PATENT DOCUMENTS

| DE | 38 23 451 | 1/1990 |
|---|---|---|
| EP | 0219027 | 4/1987 |
| WO | 2004/108894 | 12/2004 |
| WO | WO 2004/108894 A2 * | 12/2004 |

OTHER PUBLICATIONS

Haziza, C., et al., "Nucleotide sequence of the *asd* gene of *Escherichia coli*: absence of a typical attenuation signal," The EMBO Journal 1982;1(3):379-384.

Viola, R. E., "The Central Enzymes of the Aspartate Family of Amino Acid Biosynthesis," Acc. Chem. Res. 2001;34:339-349.

Chassagnole, C., et al., "An integrated study of threonine-pathway enzyme kinetics in *Escherichia coli*," Biochem. J. 2001;356:415-423.

Rais, B., et al., "Threonine synthesis from aspartate in *Escherichia coli* cell-free extracts: pathway dynamics," Biochem. J. 2001;356:425-432.

International Search Report for PCT Appl. No. PCT/JP2004/018435 (Apr. 15, 2005).

Written Opinion for PCT Appl. No. PCT/JP2004/018436 (Apr. 15, 2005).

International Preliminary Report on Patentability for PCT Patent App. No. PCT/JP2004/018436 (Jun. 15, 2006).

* cited by examiner

*Primary Examiner*—Tekchand Saidha
*Assistant Examiner*—Iqbal Chowdhury
(74) *Attorney, Agent, or Firm*—Cermak & Kenealy, LLP; Shelly Guest Cermak

(57) ABSTRACT

There is disclosed a method for producing L-threonine using bacterium belonging to the genus *Escherichia* wherein the bacterium has been modified to enhance an activity of aspartate-β-semialdehyde dehydrogenase.

5 Claims, No Drawings

SEQUENCE LISTING

<160> NUMBER OF SEQ ID NOS: 2

<210> SEQ ID NO 1
<211> LENGTH: 1104
<212> TYPE: DNA
<213> ORGANISM: Escherichia coli
<220> FEATURE:
<221> NAME/KEY: CDS
<222> LOCATION: (1)..(1104)

<400> SEQUENCE: 1

```
atg aaa aat gtt ggt ttt atc ggc tgg cgc ggt atg gtc ggc tcc gtt      48
Met Lys Asn Val Gly Phe Ile Gly Trp Arg Gly Met Val Gly Ser Val
 1               5                  10                  15 ctc atg caa cgc atg gtt gaa gag cgc gac ttc gac gcc att cgc cct      96
Leu Met Gln Arg Met Val Glu Glu Arg Asp Phe Asp Ala Ile Arg Pro
             20                  25                  30 gtc ttc ttt tct act tct cag ctt ggc cag gct gcg ccg tct ttt ggc     144
Val Phe Phe Ser Thr Ser Gln Leu Gly Gln Ala Ala Pro Ser Phe Gly
         35                  40                  45 gga acc act ggc aca ctt cag gat gcc ttt gat ctg gag gcg cta aag     192
Gly Thr Thr Gly Thr Leu Gln Asp Ala Phe Asp Leu Glu Ala Leu Lys
     50                  55                  60 gcc ctc gat atc att gtg acc tgt cag ggc ggc gat tat acc aac gaa     240
Ala Leu Asp Ile Ile Val Thr Cys Gln Gly Gly Asp Tyr Thr Asn Glu
 65                  70                  75                  80 atc tat cca aag ctt cgt gaa agc gga tgg caa ggt tac tgg att gac     288
Ile Tyr Pro Lys Leu Arg Glu Ser Gly Trp Gln Gly Tyr Trp Ile Asp
                 85                  90                  95 gca gca tcg tct ctg cgc atg aaa gat gac gcc atc atc att ctt gac     336
Ala Ala Ser Ser Leu Arg Met Lys Asp Asp Ala Ile Ile Ile Leu Asp
            100                 105                 110 ccc gtc aat cag gac gtc att acc gac gga tta aat aat ggc atc agg     384
Pro Val Asn Gln Asp Val Ile Thr Asp Gly Leu Asn Asn Gly Ile Arg
        115                 120                 125 act ttt gtt ggc ggt aac tgt acc gta agc ctg atg ttg atg tcg ttg     432
Thr Phe Val Gly Gly Asn Cys Thr Val Ser Leu Met Leu Met Ser Leu
    130                 135                 140 ggt ggt tta ttc gcc aat gat ctt gtt gat tgg gtg tcc gtt gca acc     480
Gly Gly Leu Phe Ala Asn Asp Leu Val Asp Trp Val Ser Val Ala Thr
145                 150                 155                 160
```

```
tac cag gcc gct tcc ggc ggt ggt gcg cga cat atg cgt gag tta tta       528
Tyr Gln Ala Ala Ser Gly Gly Gly Ala Arg His Met Arg Glu Leu Leu
                165                 170                 175 acc cag atg ggc cat ctg tat ggc cat gtg gca gat gaa ctc gcg acc       576
Thr Gln Met Gly His Leu Tyr Gly His Val Ala Asp Glu Leu Ala Thr
            180                 185                 190 ccg tcc tct gct att ctc gat atc gaa cgc aaa gtc aca acc tta acc       624
Pro Ser Ser Ala Ile Leu Asp Ile Glu Arg Lys Val Thr Thr Leu Thr
        195                 200                 205 cgt agc ggt gag ctg ccg gtg gat aac ttt ggc gtg ccg ctg gcg ggt       672
Arg Ser Gly Glu Leu Pro Val Asp Asn Phe Gly Val Pro Leu Ala Gly
    210                 215                 220 agc ctg att ccg tgg atc gac aaa cag ctc gat aac ggt cag agc cgc       720
Ser Leu Ile Pro Trp Ile Asp Lys Gln Leu Asp Asn Gly Gln Ser Arg
225                 230                 235                 240 gaa gag tgg aaa ggg cag gcg gaa acc aac aag atc ctc aac aca tct       768
Glu Glu Trp Lys Gly Gln Ala Glu Thr Asn Lys Ile Leu Asn Thr Ser
                245                 250                 255 tcc gta att ccg gta gat ggt tta tgt gtg cgt gtc ggg gca ttg cgc       816
Ser Val Ile Pro Val Asp Gly Leu Cys Val Arg Val Gly Ala Leu Arg
            260                 265                 270 tgc cac agc cag gca ttc act att aaa ttg aaa aaa gat gtg tct att       864
Cys His Ser Gln Ala Phe Thr Ile Lys Leu Lys Lys Asp Val Ser Ile
        275                 280                 285 ccg acc gtg gaa gaa ctg ctg gct gcg cac aat ccg tgg gcg aaa gtc       912
Pro Thr Val Glu Glu Leu Leu Ala Ala His Asn Pro Trp Ala Lys Val
    290                 295                 300 gtt ccg aac gat cgg gaa atc act atg cgt gag cta acc cca gct gcc       960
Val Pro Asn Asp Arg Glu Ile Thr Met Arg Glu Leu Thr Pro Ala Ala
305                 310                 315                 320 gtt acc ggc acg ctg acc acg ccg gta ggc cgc ctg cgt aag ctg aat      1008
Val Thr Gly Thr Leu Thr Thr Pro Val Gly Arg Leu Arg Lys Leu Asn
                325                 330                 335 atg gga cca gag ttc ctg tca gcc ttt acc gtg ggc gac cag ctg ctg      1056
Met Gly Pro Glu Phe Leu Ser Ala Phe Thr Val Gly Asp Gln Leu Leu
            340                 345                 350 tgg ggg gcc gcg gag ccg ctg cgt cgg atg ctt cgt caa ctg gcg taa      1104
Trp Gly Ala Ala Glu Pro Leu Arg Arg Met Leu Arg Gln Leu Ala
        355                 360                 365

<210> SEQ ID NO 2
<211> LENGTH: 367
<212> TYPE: PRT
<213> ORGANISM: Escherichia coli

<400> SEQUENCE: 2

Met Lys Asn Val Gly Phe Ile Gly Trp Arg Gly Met Val Gly Ser Val
1               5                   10                  15

Leu Met Gln Arg Met Val Glu Glu Arg Asp Phe Asp Ala Ile Arg Pro
            20                  25                  30

Val Phe Phe Ser Thr Ser Gln Leu Gly Gln Ala Ala Pro Ser Phe Gly
        35                  40                  45

Gly Thr Thr Gly Thr Leu Gln Asp Ala Phe Asp Leu Glu Ala Leu Lys
    50                  55                  60

Ala Leu Asp Ile Ile Val Thr Cys Gln Gly Gly Asp Tyr Thr Asn Glu
65                  70                  75                  80

Ile Tyr Pro Lys Leu Arg Glu Ser Gly Trp Gln Gly Tyr Trp Ile Asp
                85                  90                  95
```

-continued

```
Ala Ala Ser Ser Leu Arg Met Lys Asp Asp Ala Ile Ile Ile Leu Asp
        100                 105                 110

Pro Val Asn Gln Asp Val Ile Thr Asp Gly Leu Asn Asn Gly Ile Arg
        115                 120                 125

Thr Phe Val Gly Gly Asn Cys Thr Val Ser Leu Met Leu Met Ser Leu
        130                 135                 140

Gly Gly Leu Phe Ala Asn Asp Leu Val Asp Trp Val Ser Val Ala Thr
145                 150                 155                 160

Tyr Gln Ala Ala Ser Gly Gly Ala Arg His Met Arg Glu Leu Leu
                165                 170                 175

Thr Gln Met Gly His Leu Tyr Gly His Val Ala Asp Glu Leu Ala Thr
            180                 185                 190

Pro Ser Ser Ala Ile Leu Asp Ile Glu Arg Lys Val Thr Thr Leu Thr
        195                 200                 205

Arg Ser Gly Glu Leu Pro Val Asp Asn Phe Gly Val Pro Leu Ala Gly
    210                 215                 220

Ser Leu Ile Pro Trp Ile Asp Lys Gln Leu Asp Asn Gly Gln Ser Arg
225                 230                 235                 240

Glu Glu Trp Lys Gly Gln Ala Glu Thr Asn Lys Ile Leu Asn Thr Ser
                245                 250                 255

Ser Val Ile Pro Val Asp Gly Leu Cys Val Arg Val Gly Ala Leu Arg
            260                 265                 270

Cys His Ser Gln Ala Phe Thr Ile Lys Leu Lys Lys Asp Val Ser Ile
        275                 280                 285

Pro Thr Val Glu Glu Leu Leu Ala Ala His Asn Pro Trp Ala Lys Val
    290                 295                 300

Val Pro Asn Asp Arg Glu Ile Thr Met Arg Glu Leu Thr Pro Ala Ala
305                 310                 315                 320

Val Thr Gly Thr Leu Thr Thr Pro Val Gly Arg Leu Arg Lys Leu Asn
                325                 330                 335

Met Gly Pro Glu Phe Leu Ser Ala Phe Thr Val Gly Asp Gln Leu Leu
            340                 345                 350

Trp Gly Ala Ala Glu Pro Leu Arg Arg Met Leu Arg Gln Leu Ala
        355                 360                 365
```

L-THREONINE PRODUCING BACTERIUM BELONGING TO THE GENUS *ESCHERICHIA* AND METHOD FOR PRODUCING L-THREONINE

This application claims priority under 35 U.S.C. §119(e) to provisional application 60/586,222, filed on Jul. 9, 2004.

BACKGROUND OF THE INVENTION

1. Technical Field

The present invention relates to a method for producing an L-amino acid by fermentation, and more specifically to a gene derived from *Escherichia coli* which aids in this fermentation. The gene is useful for improvement of L-amino acid production, and specifically, for example, for L-threonine production.

2. Description of the Related Art

Conventionally, L-amino acids are industrially produced by fermentation methods utilizing strains of microorganisms obtained from natural sources or mutants thereof, which are modified to enhance production yields of L-amino acids.

Many techniques to enhance production yields of L-amino acids have been reported, including transformation of microorganisms with recombinant DNA (see, for example, U.S. Pat. No. 4,278,765). Other techniques for enhancing production yields include increasing the activities of enzymes involved in amino acid biosynthesis and/or desensitizing the target enzymes of the feedback inhibition by the resulting L-amino acid (see, for example, WO 95/16042 or U.S. Pat. Nos. 4,346,170, 5,661,012 and 6,040,160).

Strains useful in production of L-threonine by fermentation are known, including strains with increased activities of enzymes involved in L-threonine biosynthesis (U.S. Pat. Nos. 5,175,107; 5,661,012; 5,705,371; 5,939,307; EP0219027), strains resistant to chemicals such as L-threonine and its analogs (WO0114525A1, EP301572A2, U.S. Pat. No. 5,376,538), strains with target enzymes desensitized to feedback inhibition by the produced L-amino acid or its by-products (U.S. Pat. Nos. 5,175,107; 5,661,012), and strains with inactivated threonine degradation enzymes (U.S. Pat. Nos. 5,939,307; 6,297,031).

The known threonine-producing strain VKPM B-3996 (U.S. Pat. Nos. 5,175,107, and 5,705,371) is the best threonine producer known at present. For construction of the strain VKPM B-3996, several mutations and a plasmid, described below, were introduced into parent strain *E. coli* K-12 (VKPM B-7). Mutant thrA gene (mutation thrA442) encodes aspartokinase homoserine dehydrogenase I, which is resistant to feedback inhibition by threonine. Mutant ilvA gene (mutation ilvA442) encodes threonine deaminase having decreased activity which results in a decreased rate of isoleucine biosynthesis and to a leaky phenotype of isoleucine starvation. In bacteria containing the ilvA442 mutation, transcription of the thrABC operon is not repressed by isoleucine, and therefore is very efficient for threonine production. Inactivation of the tdh gene results in prevention of threonine degradation. The genetic determinant of saccharose assimilation (scrKYABR genes) was transferred to said strain. To increase expression of the genes controlling threonine biosynthesis, plasmid pVIC40 containing mutant threonine operon thrA442BC was introduced in the intermediate strain TDH6. The amount of L-threonine accumulated during fermentation of the strain can be up to 85 g/l.

The present inventors obtained, with respect to *E. coli* K-12, a mutant, thrR (herein referred to as rhtA23) that has resistance to high concentrations of threonine or homoserine in minimal media (Astaurova, O. B. et al., Appl. Bioch. And Microbiol., 21, 611–616 (1985)). The mutation resulted in improvement in production of L-threonine (SU Pat. No. 974817), homoserine, and glutamate (Astaurova, O. B. et al., Appl. Bioch. And Microbiol., 27, 556–561, 1991, EP 1013765 A) by the respective *E. coli* producing strain, such as the strain VKPM B-3996. Furthermore, the present inventors have revealed that the rhtA gene exists at 18 min on *E. coli* chromosome close to the glnHPQ operon that encodes components of the glutamine transport system, and that the rhtA gene is identical to ORF1 (ybiF gene, numbers 764 to 1651 in the GenBank accession number AAA218541, gi:440181), located between the pexB and ompX genes. The unit expressing a protein encoded by the ORF1 has been designated as rhtA (rht: resistance to homoserine and threonine) gene. Also, the present inventors have found that the rhtA23 mutation is an A-for-G substitution at position −1 with respect to the ATG start codon (ABSTRACTS of $17^{th}$ International Congress of Biochemistry and Molecular Biology in conjugation with 1997 Annual Meeting of the American Society for Biochemistry and Molecular Biology, San Francisco, Calif. Aug. 24–29, 1997, abstract No. 457, EP 1013765 A).

Under conditions of optimization of the mainstream threonine biosynthetic pathway, further improvement of threonine-producing strains can be accomplished by supplementing the bacterium with increasing amounts of distant precursors of threonine, such as aspartate.

It is known that aspartate is a carbon donor during synthesis of the amino acids of the aspartate family (threonine, methionine, lysine), and diaminopimelate, a compound constituent of the bacterial cell wall. These syntheses are performed by a complex pathway having several branch points and an extremely sensitive regulatory scheme. In the branch points (aspartate, aspartate semialdehyde, homoserine), there are as many isozymes as there are amino acids deriving from this biosynthetic step. The aspartokinase homoserine dehydrogenase I encoded by part of thrABC operon causes the first and third reactions of threonine biosynthesis. Threonine and isoleucine regulate the expression of aspartokinase homoserine dehydrogenase I, and threonine inhibits both activities to catalyze the above-described reactions (*Escherichia coli* and *Salmonella*, Second Edition, Editor in Chief: F. C. Neidhardt, ASM Press, Washington D.C., 1996).

The asd gene encodes aspartate-β-semialdehyde dehydrogenase (Asd; EC 1.2.1.11), which is a key enzyme in the biosynthetic pathways for lysine, methionine, threonine and diaminopimelate. Aspartate-β-semialdehyde dehydrogenase reversibly converts L-aspartyl-4-P to L-aspartate semialdehyde along with the reduction of NADP. The effect of amplification of the asd gene on production of L-lysine, an amino acid of aspartate family, by *E. coli* strain is disclosed (U.S. Pat. No. 6,040,160). It has also been disclosed that aspartate-β-semialdehyde dehydrogenase could be useful for production of L-lysine, L-threonine and L-isoleucine by coryneform bacteria (European patent application 0219027).

However, there has been no report to date of using a bacterium belonging to the genus *Escherichia* with enhanced aspartate-β-semialdehyde dehydrogenase activity for the production of L-threonine.

SUMMARY OF THE INVENTION

An object of present invention is to enhance the productivity of L-threonine-producing strains and to provide a method for producing L-threonine using these strains.

This aim was achieved by finding that the asd gene encoding aspartate-β-semialdehyde dehydrogenase cloned on a low copy vector enhances L-threonine production. Thus the present invention has been completed.

It is an object of the present invention to provide an L-threonine-producing bacterium belonging to the genus *Escherichia*, wherein said bacterium has been modified to enhance an activity of aspartate-β-semialdehyde dehydrogenase.

It is a further object of the present invention to provide the bacterium described above, wherein the activity of aspartate-β-semialdehyde dehydrogenase is enhanced by increasing the expression of an aspartate-β-semialdehyde dehydrogenase gene.

It is a further object of the present invention to provide the bacterium described above, wherein said activity of aspartate-β-semialdehyde dehydrogenase is enhanced by increasing the copy number of the aspartate-β-semialdehyde dehydrogenase gene or modifying an expression control sequence of the gene so that the gene expression is enhanced.

It is a further object of the present invention to provide the bacterium as described above, wherein the copy number is increased by transformation of the bacterium with a vector containing the gene.

It is a further object of the present invention to provide the bacterium as described above, wherein the aspartate-β-semialdehyde dehydrogenase gene is derived from a bacterium belonging to the genus *Escherichia*.

It is a further object of the present invention to provide the bacterium as described above, wherein said aspartate-β-semialdehyde dehydrogenase gene encodes a protein selected from the group consisting of:

(A) a protein which comprises the amino acid sequence of SEQ ID NO: 2; and (B) a protein, which comprises an amino acid sequence including deletion, substitution, insertion or addition of one or several amino acids in the amino acid sequence of SEQ ID NO: 2, and which has an activity of aspartate-β-semialdehyde dehydrogenase.

It is a further object of the present invention to provide the bacterium as described above, wherein the aspartate-β-semialdehyde dehydrogenase gene comprises a DNA selected from the group consisting of:

(a) a DNA which comprises a nucleotide sequence of nucleotides 1 to 1101 in SEQ ID NO: 1; and (b) a DNA which is hybridizable with a nucleotide sequence of nucleotides 1–1101 in SEQ ID NO: 1, or a probe which can be prepared from said nucleotide sequence under stringent conditions, and encodes a protein having an activity of aspartate-β-semialdehyde dehydrogenase.

It is a further object of the present invention to provide the bacterium as described above, wherein said stringent conditions comprise those in which washing is performed at 60° C. at a salt concentration of 1×SSC and 0.1% SDS, and for 15 minutes.

It is a further object of the present invention to provide the bacterium as described above, wherein said bacterium has been further modified to enhance expression of one or more of the genes selected from the group consisting of the mutant thrA gene which codes for aspartokinase homoserine dehydrogenase I and is resistant to feedback inhibition by threonine;

the thrB gene which codes for homoserine kinase;

the thrC gene which codes for threonine synthase; and the rhtA gene which codes for a putative transmembrane protein.

It is a further object of the present invention to provide the bacterium as described above, wherein said bacterium has been modified to increase expression of said mutant thrA gene, said thrB gene, said thrC gene and said rhtA gene.

It is a further object of the present invention to provide a method for producing L-threonine which comprises cultivating the bacterium as described above in a culture medium to cause accumulatation of L-threonine in the culture medium, and collecting the L-threonine from the culture medium.

DESCRIPTION OF THE PREFERRED EMBODIMENTS

In the present invention, "L-threonine-producing bacterium" means a bacterium which has an ability to cause accumulation of L-threonine in a medium when the bacterium is cultured in the medium. The L-threonine-producing ability may be imparted or enhanced by breeding. The phrase "L-threonine-producing bacterium" as used herein also means a bacterium which is able to produce and cause accumulation of L-threonine in a culture medium in amount larger than a wild-type or parental strain of *E. coli*, such as *E. coli* K-12 strain.

The phrase "a bacterium belonging to the genus *Escherichia*" means that the bacterium is classified in the genus *Escherichia* according to the classification known to a person skilled in the art of microbiology. Examples of an microorganism belonging to the genus *Escherichia* as used in the present invention include but are not limited to *Escherichia coli* (*E. coli*).

The bacterium belonging to the genus *Escherichia* that can be used in the present invention is not particularly limited, however for example, bacteria described by Neidhardt, F. C. et al. (*Escherichia coli* and *Salmonella typhimurium*, American Society for Microbiology, Washington D.C., 1208, Table 1) are encompassed by the present invention.

The phrase "activity of aspartate-β-semialdehyde dehydrogenase" means an activity which catalyzes the reversible substrate-dependent reduction of NADP in the presence of phosphate or arsenate. Activity of aspartate-β-semialdehyde dehydrogenase can be measured by the method described by, for example, Preiss, J. et al (Curr. Microbiol., 7: 263–268 (1982)).

The phrase "modified to enhance an activity of aspartate-β-semialdehyde dehydrogenase" means that the activity per cell is higher than that of a non-modified strain, for example, a wild-type strain. Examples of such modifications include increasing the number of aspartate-β-semialdehyde dehydrogenase molecules per cell, increasing the specific activity per aspartate-β-semialdehyde dehydrogenase molecule, and so forth. Furthermore, a wild-type strain that may be used for comparison purposes includes, for example, *Escherichia coli* K-12. As a result of enhancement of intracellular activity of aspartate-β-semialdehyde dehydrogenase, the amount of L-threonine accumulation in a medium increases.

Enhancement of aspartate-β-semialdehyde dehydrogenase activity in a bacterial cell can be attained by enhancement of expression of a gene encoding aspartate-β-semialdehyde dehydrogenase. Any gene derived from bacteria belonging to the genus *Escherichia*, as well as any gene derived from other bacteria, such as coryneform bacteria, may be used as the aspartate-β-semialdehyde dehydrogenase gene. Among these, genes derived from bacteria belonging to the genus *Escherichia* are preferred.

As the gene coding for aspartate-β-semialdehyde dehydrogenase of *Escherichia coli*, asd gene has already been elucidated (nucleotide numbers 3572511 to 3571408 in the sequence of GenBank accession NC_000913.1, gi: 16131307). Therefore, the asd gene can be obtained by PCR (polymerase chain reaction; refer to White, T. J. et al., *Trends Genet.*, 5, 185 (1989)) utilizing primers prepared based on the nucleotide sequence of the gene. Genes coding for aspartate-β-semialdehyde dehydrogenase of other microorganisms can be obtained in a similar manner.

The asd gene derived from *Escherichia coli* is exemplified by a DNA which encodes the following protein (A) or (B):

(A) a protein which has the amino acid sequence shown in SEQ ID NO: 2; or (B) a protein which has an amino acid sequence including deletion, substitution, insertion or addition of one or several amino acids in the amino acid sequence shown in SEQ ID NO: 2, and which has an activity of aspartate semialdehyde dehydrogenase.

The number of "several" amino acids differs depending on the position or the type of amino acid residues in the three dimensional structure of the protein. It may be 2 to 30, preferably 2 to 15, and more preferably 2 to 5 for the protein (A). The deletion, substitution, insertion or addition of amino acids can occur in regions of the protein which are not critical for the function of the protein. This is because some amino acids have high homology to one another so the three dimensional structure or activity is not affected by such a change. Therefore, the protein variant (B) may be one which has homology of not less than 70%, preferably not less than 80%, more preferably not less than 90%, and most preferably not less than 95% with respect to the entire amino acid sequence of aspartate-β-semialdehyde dehydrogenase shown in SEQ ID NO: 2, as long as the activity of aspartate-β-semialdehyde dehydrogenase is maintained. Homology between two amino acid sequences can be determined using the well-known methods, for example, the computer program BLAST 2.0, which calculates three parameters: score, identity and similarity.

The substitution, deletion, insertion or addition of one or several amino acid residues should be conservative mutation(s) so that the activity is maintained. The representative conservative mutation is a conservative substitution. Examples of conservative substitutions include substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val.

The DNA, which encodes substantially the same protein as the aspartate-β-semialdehyde dehydrogenase described above, may be obtained, for example, by modifying the nucleotide sequence of DNA encoding aspartate-β-semialdehyde dehydrogenase (SEQ ID NO: 1), for example, by means of the site-directed mutagenesis method so that one or more amino acid residues at a specified site involve deletion, substitution, insertion, or addition. DNA modified as described above may be obtained by conventionally known mutation treatments. Such treatments include hydroxylamine treatment of the DNA encoding proteins of present invention, or treatment of the bacterium containing the DNA with UV irradiation or a reagent such as N-methyl-N'-nitro-N-nitrosoguanidine or nitrous acid.

A DNA encoding substantially the same protein as aspartate-β-semialdehyde dehydrogenase can be obtained by expressing DNA having the mutation as described above in an appropriate cell, and investigating the activity of any expressed product. A DNA encoding substantially the same protein as aspartate-β-semialdehyde dehydrogenase can also be obtained by isolating a DNA from mutant DNA encoding aspartate-β-semialdehyde dehydrogenase or from a mutant-containing cell, that is hybridizable with a probe having a nucleotide sequence which contains, for example, the nucleotide sequence shown as SEQ ID NO: 1, under the stringent conditions, and encodes a protein having the aspartate-β-semialdehyde dehydrogenase activity. The "stringent conditions" referred to herein are conditions under which so-called specific hybrids are formed, and non-specific hybrids are not formed. It is difficult to clearly express this condition by using any numerical value. However, for example, stringent conditions can be exemplified by conditions under which DNAs having high homology, for example, DNAs having homology of not less than 50% are able to hybridize with each other, but DNAs having homology lower than the above are not able to hybridize with each other. Alternatively, stringent conditions may be exemplified by conditions under which DNA is able to hybridize at a salt concentration equivalent to ordinary washing conditions in Southern hybridization, i.e., 1×SSC, 0.1% SDS, preferably 0.1×SSC, 0.1% SDS, at 60° C. Duration of washing depends on the type of membrane used for blotting and, as a rule, is recommended by manufacturer. For example, recommended duration of washing the Hybond™ N+ nylon membrane (Amersham) under stringent conditions is 15 minutes.

A partial sequence of the nucleotide sequence of SEQ ID NO: 1 can also be used as a probe. Probes may be prepared by PCR using primers based on the nucleotide sequence of SEQ ID NO: 1, and a DNA fragment containing the nucleotide sequence of SEQ ID NO: 1 as a template. When a DNA fragment having a length of about 300 bp is used as the probe, the hybridization conditions for washing include, for example, 50° C., 2×SSC and 0.1% SDS.

The substitution, deletion, insertion, or addition of nucleotides as described above also includes mutation, which naturally occurs (mutant or variant), for example, due to variety in the species or genus of bacterium, which contains the aspartate-β-semialdehyde dehydrogenase.

"Transformation of a bacterium with DNA encoding a protein" means introduction of the DNA into a bacterium, for example, by conventional methods. Transformation of this DNA will result in an increase in expression of the gene encoding the protein of present invention, and will enhance the activity of the protein in the bacterial cell.

Methods of gene expression enhancement include increasing the gene copy number. Introducing a gene into a vector that is able to function in a bacterium belonging to thegenus *Escherichia* increases the copy number of the gene.

Preferably, low copy vectors are used. Examples of low-copy vectors include but are not limited to pSC101, pMW118, pMW119, and the like. The term "low copy vector" is used for vectors, the copy number of which is up to 5 copies per cell. Methods of transformation include any known methods that have hitherto been reported. For example, a method of treating recipient cells with calcium chloride so as to increase permeability of the cells to DNA has been reported for *Escherichia coli* K-12 (Mandel, M. and Higa, A., *J. Mol. Biol.*, 53, 159 (1970)) and may be used.

Enhancement of gene expression may also be achieved by introduction of multiple copies of the gene into a bacterial chromosome by, for example, a method of homologous recombination, Mu integration or the like. For example, one act of Mu integration allows introduction into the bacterial chromosome of up to 3 copies of the gene.

Enhancement of gene expression may also be achieved by placing the DNA of the present invention under the control of a potent promoter. For example, the lac promoter, the trp promoter, the trc promoter, and the $P_R$, and the $P_L$ promoters of lambda phage are known as potent promoters. Use of a potent promoter can be combined with multiplication of gene copies.

Alternatively, the effect of a promoter can be enhanced by, for example, introducing a mutation into the promoter to increase a transcription level of a gene located downstream of the promoter. Furthermore, it is known that substitution of several nucleotides in the spacer between ribosome binding site (RBS) and the start codon, especially the sequences immediately upstream of the start codon, profoundly affect the mRNA translatability. For example, a 20-fold range in the expression levels was found, depending on the nature of the three nucleotides preceding the start codon (Gold et al., Annu. Rev. Microbiol., 35, 365–403, 1981; Hui et al., EMBO J., 3, 623–629, 1984). Previously, it was shown that the rhtA23 mutation is an A-for-G substitution at the −1 position relative to the ATG start codon (ABSTRACTS of 17$^{th}$ International Congress of Biochemistry and Molecular Biology in conjugation with 1997 Annual Meeting of the American Society for Biochemistry and Molecular Biology, San Francisco, Calif. Aug. 24–29, 1997, abstract No. 457). Therefore, it may be suggested that the rhtA23 mutation enhances the rhtA gene expression and, as a consequence, increases the resistance to threonine, homoserine and some other substances transported out of cells.

Moreover, it is also possible to introduce a nucleotide substitution into a promoter region of the aspartate-β-semialdehyde dehydrogenase gene on the bacterial chromosome resulting in a stronger promoter function. The alteration of the expression control sequence can be performed, for example, in the same manner as the gene substitution using a temperature-sensitive plasmid, as disclosed in International Publication WO00/18935 and Japanese Patent Publication No. 1-215280.

Increasing the copy number of the aspartate-β-semialdehyde dehydrogenase gene can also be achieved by introducing multiple copies of the aspartate-β-semialdehyde dehydrogenase gene into the chromosomal DNA of the bacterium. In order to introduce multiple copies of the aspartate-β-semialdehyde dehydrogenase gene into bacterial chromosome, homologous recombination is carried out using a sequence whose multiple copies exist as targets in the chromosomal DNA. Sequences having multiple copies in the chromosomal DNA include, but are not limited to repetitive DNA, or inverted repeats existing at the end of a transposable element. Also, as disclosed in U.S. Pat. No. 5,595,889, it is possible to incorporate the aspartate-β-semialdehyde dehydrogenase gene into a transposon, and allow it to be transferred to introduce multiple copies of the gene into the chromosomal DNA.

Methods for preparation of plasmid DNA include, but are not limited to digestion and ligation of DNA, transformation, selection of an oligonucleotide as a primer and the like, or other methods well known to one skilled in the art. These methods are described, for instance, in Sambrook, J., Fritsch, E. F., and Maniatis, T., "Molecular Cloning A Laboratory Manual, Second Edition", Cold Spring Harbor Laboratory Press (1989).

The bacterium of the present invention can be obtained by introduction of the aforementioned DNAs into bacterium which inherently has the ability to produce L-threonine. Alternatively, the bacterium of the present invention can be obtained by imparting an ability to produce L-threonine to the bacterium already containing the DNAs.

Examples of parent strains encompassed by the present invention include, but are not limited to the threonine-producing bacteria belonging to the genus *Escherichia* such as *E. coli* strain TDH-6/pVIC40 (VKPM B-3996) (U.S. Pat. Nos. 5,175,107, 5,705,371), *E. coli* strain NRRL-21593 (U.S. Pat. No. 5,939,307), *E. coli* strain FERM BP-3756 (U.S. Pat. No. 5,474,918), *E. coli* strains FERM BP-3519 and FERM BP-3520 (U.S. Pat. No. 5,376,538), *E. coli* strain MG442 (Gusyatiner et al., Genetika (in Russian), 14, 947–956 (1978)), *E. coli* strains VL643 and VL2055 (EP 1149911 A), and the like.

The strain TDH-6 is deficient in the thrC gene, as well as being sucrose-assimilative, and the ilvA gene has a leaky mutation. This strain has a mutation in the rhtA gene, which imparts resistance to high concentrations of threonine or homoserine. The strain B-3996 contains the plasmid pVIC40 which had been obtained by inserting thrA*BC operon including mutant thrA gene encoding aspartokinase homoserine dehydrogenase I which has substantially desensitized feedback inhibition by threonine into RSF1010-derived vector. The strain B-3996 was deposited on Nov. 19, 1987 in All-Union Scientific Center of Antibiotics (Nagatinskaya Street 3-A, 113105 Moscow, Russian Federation) under the accession number RIA 1867. The strain was also deposited on Apr. 7, 1987 in Russian National Collection of Industrial Microorganisms (VKPM) (Dorozhny proezd. 1, Moscow 113545, Russian Federation) under the accession number B-3996.

Preferably, the bacterium of the present invention is further modified to enhance expression of one or more of the following genes as well as asd gene:
  the mutant thrA gene which codes for aspartokinase homoserine dehydrogenase I resistant to feed back inhibition by threonine;
  the thrB gene which codes for homoserine kinase;
  the thrC gene which codes for threonine synthase;

Another preferred embodiment of the present invention is the bacterium modified to enhance the rhtA gene which codes for a putative transmembrane protein in addition to enhancement of asd gene. The most preferred embodiment of the present invention is a bacterium modified to increase expression of the asd gene, the mutant thrA gene, the thrB gene, the thrC gene and the rhtA gene.

The method for producing L-threonine of the present invention includes the steps of cultivating the bacterium of the present invention in a culture medium, allowing L-threonine to accumulate in the culture medium, and collecting L-threonine from the culture medium.

In the present invention, the cultivation, collection and purification of L-threonine from the medium and the like may be performed in a manner similar to conventional fermentation methods wherein L-threonine is produced using a microorganism.

A medium used for culture may be either a synthetic or natural medium, so long as the medium includes a carbon source and a nitrogen source and minerals and, if necessary, appropriate amounts of nutrients which the microorganism requires for growth. The carbon source may include various carbohydrates such as glucose and sucrose, and various organic acids. Depending on the mode of assimilation of the chosen microorganism, alcohol including ethanol and glycerol may be used. As the nitrogen source, various ammonium salts such as ammonia and ammonium sulfate, other nitrogen compounds such as amines, a natural nitrogen source such as peptone, soybean-hydrolysate, and digested fermentative microorganism are used. As minerals, potassium monophosphate, magnesium sulfate, sodium chloride, ferrous sulfate, manganese sulfate, calcium chloride, and the like are used. As vitamins, thiamine, yeast extract and the like are used. Additional nutrients can be added to the medium, if necessary. For example, if the microorganism requires isoleucine for growth (isoleucine auxotrophy), a sufficient amount of isoleucine can be added to the cultivation medium.

The cultivation is performed preferably under aerobic conditions such as a shaking culture, and stirring culture with aeration, at a temperature of 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, an 1 to 5-day cultivation leads to accumulation of L-threonine in the liquid medium.

After cultivation, solids such as cells can be removed from the liquid medium by centrifugation or membrane filtration, and then L-threonine can be collected and purified by ion-exchange, concentration and crystallization methods.

EXAMPLES

The present invention will be more concretely explained below with reference to the following non-limiting examples.

Example 1

Cloning of asd Gene from E. coli into pM Vector

The asd gene was cloned from chromosomal DNA of the E. coli strain (K12 Mu cts62 Mud5005) (VKPM B-6804) obtained from Russian National Collection of Industrial Microorganisms (VKPM) (Dorozhny proezd. 1, Moscow 113545, Russian Federation). First, mini-Mu phage in the E. coli strain (K12 Mu cts62 Mud5005) (VKPM B-6804) was induced. Then, the set of obtained derivatives of plasmids pMud5005 containing parts of chromosome was used for transformation of asd⁻ strain SH 309. The strain SH 309 (VKPM B-3899) obtained from Russian National Collection of Industrial Microorganisms (VKPM) (Dorozhny proezd. 1, Moscow 113545, Russian Federation) has the following phenotype: F⁻ araD139 rpsL150 deoC1 ptsF25 relA1 feb5301 rbsR ugpA704:Tn10 Del (argF-lac) U169 Del (mal-asd) $Tet^R$ $Str^R$. The asd⁻ strain SH 309 cannot grow on L-medium and requires diaminopimelinic acid (DAPA) for growth. SH 309 asd⁺ clones harboring plasmid pMud5005-asd were selected on the L-medium. The plasmid pMud5005-asd was isolated and BamHI-PstI DNA fragment (1646 bp) containing asd gene was recloned into the plasmid pMW119 previously modified to substitute promoter $P_{lac}$ by promoter $P_R$. Thus the plasmid pMW-asd containing the asd gene under the control of promoter $P_R$ was constructed. The plasmid pMW-asd is compatible with plasmid pVIC40 (replicon pRSF 1010), therefore the two plasmids pVIC40 and pMW-asd could be maintained in the bacteria simultaneously.

The pMW-asd plasmid was introduced into the streptomycin-resistant threonine producer E. coli strain B-3996. Thus, the strain B-3996(pMW-asd) was obtained.

Example 2

Effect of the asd Gene Amplification on Threonine Production

Both E. coli strains B-3996 and B-3996(pMW-asd) were grown for 18–24 hours at 37° C. on L-agar plates containing streptomycin (100 μg/ml) and ampicillin (100 μg/ml). To obtain seed culture, the strain was grown on a rotary shaker (250 rpm) at 32° C. for 18 hours in 20×200 mm test tubes containing 2 ml of L-broth with 4% sucrose. Then, the fermentation medium was inoculated with 0.1 ml (5%) seed material. The fermentation was performed in 2 ml of minimal medium for fermentation in 20×200 mm test tubes. Cells were grown for 24 hours at 32° C. with shaking at 250 rpm.

After cultivation, the amount of accumulated L-threonine in the medium was determined by TLC. Sorbfil plates (Stock Company Sorbopolymer, Krasnodar, Russia) were developed with a mobile phase: propan-2-ol:acetone:water:25% aqueous ammonia=25:25:7:6 (v/v). A solution (2%) of ninhydrin in acetone was used as a visualizing reagent. The results are presented in Table 1.

The composition of the fermentation medium (g/l) is as follows:

| | |
|---|---|
| Sucrose | 40.0 |
| $(NH_4)_2SO_4$ | 10.0 |
| $KH_2PO_4$ | 1.0 |
| $MgSO_4.7H_2O$ | 0.4 |
| $FeSO_4.7H_2O$ | 0.02 |
| $MnSO_4.5H_2O$ | 0.02 |
| Thiamine HCl | 0.0002 |
| Yeast extract | 1.0 |
| $CaCO_3$ | 20.0 |
| L-Isoleucine | 0.05 |

Sucrose and magnesium sulfate are sterilized separately. $CaCO_3$ is dry-heat sterilized at 180° C. for 2 h. The pH is adjusted to 7.0. Antibiotic is introduced into the medium after sterilization.

While the invention has been described in detail with reference to preferred embodiments thereof, it will be apparent to one skilled in the art that various changes can be made, and equivalents employed, without departing from the scope of the invention. Each of the aforementioned documents, including the foreign priority document RU2003135292, is incorporated by reference herein in its entirety.

TABLE 1

| Strain | OD$_{560}$ | Threonine, g/l |
|---|---|---|
| B3996/pMW-asd | 8.6 | 18.5 |
| | 8.4 | 18.3 |
| | 9.1 | 19.8 |
| | 9.5 | 19.2 |
| | 9.3 | 20.0 |
| | 8.9 | 18.6 |
| | 9.4 | 19.3 |
| | 9.0 | 19.3 |
| | 9.0 ± 0.4 | 19.1 ± 0.6 |
| B-3996 (control) | 9.3 | 18.6 |
| | 9.6 | 17.9 |
| | 10.5 | 17.9 |
| | 10.6 | 17.6 |
| | 9.8 | 17.8 |
| | 9.9 | 18.1 |
| | 10.2 | 18.0 |
| | 10.0 | 17.9 |
| | 10.0 ± 0.4 | 18.0 ± 0.3 |

We claim:

1. A method for producing L-threonine which comprises cultivating an L-threonine-producing bacterium belonging to the genus *Escherichia* wherein said bacterium has been modified to increase expression of an aspartate-β-semialdehyde dehydrogenase gene, in a culture medium to cause accumulation of L-threonine in the culture medium, and collecting the L-threonine from the culture medium, wherein said aspartate-β-semialdehyde dehydrogenase gene comprises a DNA selected from the group consisting of:
(a) a DNA which comprises the nucleotide sequence of nucleotides 1 to 1101 in SEQ ID NO: 1; and
(b) a DNA which is hybridizable with the nucleotide sequence of nucleotides 1–1101 in SEQ ID NO: 1 under stringent conditions comprising washing at 60° C. at a salt concentration of 1×SSC and 0.1% SDS for 15 minutes, and wherein said DNA encodes a protein having an activity of aspartate-β-semialdehyde dehydrogenase, wherein said bacterium has been further modified to increase expression of the mutant thrA gene which codes for aspartokinase homoserine dehydrogenase I which is resistant to feedback inhibition by threonine, the thrB gene which codes for homoserine kinase, the thrC gene which codes for threonine synthase, and the rhtA gene which codes for a putative transmembrane protein, and wherein the mutant thrA gene, the ThrB gene, the thrC gene, and the rhtA gene are genes of *Escherichia coli*.

2. The method according to claim 1, wherein the expression of the aspartate-β-semialdehyde dehydrogenase gene is increased by increasing the copy number of the aspartate-β-semialdehyde dehydrogenase gene or modifying an expression control sequence of the gene so that the gene expression is enhanced.

3. The method according to claim 2, wherein the copy number is increased by transformation of the bacterium with a vector containing the gene.

4. The method according to claim 1, wherein the aspartate-β-semialdehyde dehydrogenase gene is obtained from a bacterium belonging to the genus *Escherichia*.

5. The method according to claim 4, wherein said aspartate-β-semialdehyde dehydrogenase gene encodes a protein selected from the group consisting of:

(A) a protein which comprises the amino acid sequence of SEQ ID NO:2; and (B) a protein, which comprises an amino acid sequence including deletion, substitution, insertion or addition of one or several amino acids in the amino acid sequence of SEQ ID NO:2, wherein said protein is at least 95% homologous to SEQ ID NO: 2, and which has an activity of aspartate-β-semialdehyde dehydrogenase.

* * * * *

UNITED STATES PATENT AND TRADEMARK OFFICE
CERTIFICATE OF CORRECTION

PATENT NO. : 7,186,531 B2
APPLICATION NO. : 11/002072
DATED : March 6, 2007
INVENTOR(S) : Akhverdian et al.

It is certified that error appears in the above-identified patent and that said Letters Patent is hereby corrected as shown below:

Please replace claims 1 and 2 with the following:

Col. 15
1. A method for producing L- threonine which comprises cultivating an L-threonine-producing bacterium belonging to the genus *Escherichia* wherein said bacterium has been modified to increase expression of an aspartate-β-semialdehyde dehydrogenase gene, in a culture medium to cause accumulation of L-threonine in the culture medium, and collecting the L-threonine from the culture medium, wherein said aspartate-β-semialdehyde dehydrogenase gene comprises a DNA selected from the group consisting of:

(a) a DNA which comprises a nucleotide sequence of nucleotides 1 to 1101 in SEQ ID NO: 1; and (b) a DNA which is hybridizable with a nucleotide sequence of nucleotides 1-1101 in SEQ ID NO:1 under stringent conditions comprising washing at 60°C at a salt concentration of 1 X SSC and 0.1% SDS for 15 minutes, and wherein said DNA encodes a protein having an activity of aspartate-β-semialdehyde dehydrogenase, wherein said bacterium has been further modified to increase expression of the mutant thrA gene which codes for aspartokinase homoserine dehydrogenase I which is resistant to feedback inhibition by threonine, the thrB gene which codes for homoserine kinase, the thrC gene which codes for threonine synthase, and the rhtA gene which codes for a putative transmembrane protein, and wherein the mutant thrA gene, the thrB gene, the thrC gene, and the rhtA gene are genes of *Escherichia coli*.

UNITED STATES PATENT AND TRADEMARK OFFICE
CERTIFICATE OF CORRECTION

PATENT NO. : 7,186,531 B2
APPLICATION NO. : 11/002072
DATED : March 6, 2007
INVENTOR(S) : Akhverdian et al.

It is certified that error appears in the above-identified patent and that said Letters Patent is hereby corrected as shown below:

Col. 16
2. The method according to claim 1, wherein the expression of the aspartate-β-semialdehyde dehydrogenase gene is increased by increasing the copy number of the aspartate-β-semialdehyde dehydrogenase gene or modifying an expression control sequence of the gene so that the gene expression is enhanced.

Signed and Sealed this

Fifth Day of June, 2007

JON W. DUDAS
*Director of the United States Patent and Trademark Office*